US007018640B2

(12) United States Patent
Evans et al.

(10) Patent No.: US 7,018,640 B2
(45) Date of Patent: *Mar. 28, 2006

(54) IN OVO VACCINATION AGAINST COCCIDIOSIS

(75) Inventors: Nigel A. Evans, East Lyme, CT (US); Robert Craig Findly, Wethersfield, CT (US); Frederick H. Weber, Terre Haute, IN (US)

(73) Assignee: Pfizer Incorporated, New York, NY (US)

( * ) Notice: Subject to any disclaimer, the term of this patent is extended or adjusted under 35 U.S.C. 154(b) by 714 days.

This patent is subject to a terminal disclaimer.

(21) Appl. No.: 10/094,436

(22) Filed: Mar. 8, 2002

(65) Prior Publication Data
US 2002/0146435 A1 Oct. 10, 2002

Related U.S. Application Data

(63) Continuation of application No. 08/973,133, filed as application No. PCT/IB95/00446 on Jun. 7, 1995, now Pat. No. 6,500,438.

(51) Int. Cl.
A61K 39/00 (2006.01)
A61K 39/38 (2006.01)
A61K 39/012 (2006.01)
A61K 39/002 (2006.01)
A61K 39/008 (2006.01)

(52) U.S. Cl. .............. 424/267.1; 424/184.1; 424/265.1; 424/93.1; 424/93.21; 424/271.1; 424/269.1; 435/242; 435/243; 435/258.1; 435/258.4

(58) Field of Classification Search ............ 424/265.1, 424/184.1, 93.1, 267.1, 271.1, 173.1, 193.1, 424/93.21, 269.1; 435/242, 243, 252.1, 235, 435/258.1, 258.4
See application file for complete search history.

(56) References Cited

U.S. PATENT DOCUMENTS

| 4,040,388 A | 8/1977 | Miller |
| 4,301,148 A | 11/1981 | Shibata et al. ............... 424/93 |
| 4,357,320 A | 11/1982 | Apontoweil et al. .......... 424/89 |
| 4,438,097 A | 3/1984 | Shirley |
| 4,458,630 A | 7/1984 | Sharma et al. ................. 119/1 |
| 4,469,047 A | 9/1984 | Miller ........................... 119/1 |
| 4,500,638 A | 2/1985 | Apontoweil et al. ........ 435/235 |
| 4,505,892 A | 3/1985 | Apontoweil et al. .......... 424/89 |
| 4,544,548 A | 10/1985 | Davis et al. |
| 4,593,646 A | 6/1986 | Miller et al. |
| 4,650,676 A | 3/1987 | Schenkel et al. .............. 424/88 |
| 4,681,063 A | 7/1987 | Hebrank |
| 4,735,801 A | 4/1988 | Stocker ........................ 424/92 |
| 4,751,079 A | 6/1988 | Burger et al. ................. 424/89 |
| 4,808,404 A | 2/1989 | Bhogal .......................... 424/88 |
| 4,935,007 A | 6/1990 | Bafundo et al. |
| 5,004,607 A | 4/1991 | Ragland et al. ............... 424/88 |
| 5,006,341 A | 4/1991 | Davis et al. ................. 424/442 |
| 5,028,421 A | 7/1991 | Fredericksen et al. ..... 424/85.2 |
| 5,055,292 A | 10/1991 | McDonald et al. |
| 5,068,104 A | 11/1991 | Bhogal et al. ................ 424/88 |
| 5,106,617 A | 4/1992 | Federicksen et al. ...... 424/85.2 |
| 5,279,960 A | 1/1994 | Anderson et al. ........... 435/243 |
| 5,288,845 A | 2/1994 | Chakraborty et al. .... 536/24.32 |
| 5,311,841 A | 5/1994 | Thaxton ...................... 604/51 |
| 5,339,766 A | 8/1994 | Phelps et al. ................ 119/6.8 |
| 5,359,050 A | 10/1994 | Chakraborty et al. .... 536/24.32 |
| 5,661,015 A | 8/1997 | Binger et al. |
| 5,674,484 A | 10/1997 | Miller et al. |
| 5,807,551 A | 9/1998 | Reynolds |
| 5,843,722 A | 12/1998 | Bumstead et al. ......... 435/69.3 |
| 5,846,527 A | 12/1998 | Miller et al. ................ 424/93.1 |
| 5,932,225 A | 8/1999 | Wallach et al. ........... 424/267.1 |
| 6,019,985 A | 2/2000 | Brown et al. |
| 6,048,535 A * | 4/2000 | Sharma .................... 424/202.1 |
| 6,231,871 B1 | 5/2001 | Coloe |
| 6,495,146 B1 * | 12/2002 | Evans et al. .............. 424/265.1 |
| 6,500,438 B1 * | 12/2002 | Evans et al. .............. 424/271.1 |
| 6,608,033 B1 * | 8/2003 | Canning et al. ............... 514/29 |
| 6,627,205 B1 * | 9/2003 | Evans et al. .............. 424/267.1 |
| 6,890,527 B1 * | 5/2005 | Thoma et al. ............. 424/93.1 |
| 6,908,620 B1 * | 6/2005 | McDougald et al. ..... 424/267.1 |
| 2004/0214782 A1 * | 10/2004 | Canning et al. ............... 514/28 |

FOREIGN PATENT DOCUMENTS

| CA | 2098773 | 12/1994 |
| EP | 047662 | 12/1987 |
| EP | 256878 | 2/1988 |
| EP | 258045 | 3/1988 |
| EP | 291173 | 11/1988 |
| EP | 344808 | 12/1989 |
| EP | 109942 | 3/1991 |
| EP | 439056 | 7/1991 |
| EP | 522482 | 1/1993 |
| EP | 650733 | 5/1995 |

(Continued)

OTHER PUBLICATIONS

Danforth et al, International J. Parasitology, 1998, 28:1099-1109.*

(Continued)

Primary Examiner—N. M. Minnifield
(74) Attorney, Agent, or Firm—Myers Bigel Sibley & Sajovec, P.A.

(57) ABSTRACT

The invention relates to a method of vaccinating a domesticated bird against coccidiosis comprising administering in ovo an effective immnunizing dose of live *Eimeria* sporozoites or merozoites, or a mixture thereof. In a preferred embodiment, the domesticated bird that is vaccinated is a chicken or turkey.

24 Claims, No Drawings

FOREIGN PATENT DOCUMENTS

| | | |
|---|---|---|
| JP | 4932381 | 9/1979 |
| JP | 2573189 | 4/1988 |
| JP | 1313437 | 12/1989 |
| NL | 8802399 | 4/1990 |
| WO | WO 9301276 | 1/1993 |
| WO | WO 9416725 | 8/1994 |
| WO | WO 9640234 | 12/1996 |
| WO | WO 9712582 | 4/1997 |
| WO | WO 9814212 | 4/1998 |
| WO | WO 8808699 | 11/1998 |

OTHER PUBLICATIONS

Vermeulen, International J. Parasitology, 1998, 28:1121-1130.*

Jenkins, International J. Parasitology, 1998, 28:1111-1119.*

Cox, International J. Parasitology, 1998, 28:165-179.*

Smith et al, Parasitology Today, 1998, 14/6:215-218.*

Augustine et al, TRENDS in Parasitology, 2001, 17/11:509-511.*

Chapman et al, International J. Parasitology, 2002, 32:617-629.*

Dalloul et al, Vaccine, 2005, In Press 6 pages.*

Vermeulen et al, Vet. Parasitology, 2001, 100/1-2:13-20.*

LeMay et al, 2001, Conference Abstract.*

Barriga, Vet. Parasitology, 1994, 55/1-2:29-55.*

Ding et al, Vaccine, 2005, In Press, 8 pages.*

Ding et al, Infection and Immunity, 2004, 72/12:6939-6944.*

Smith et al, Infection and Immunity, 1994, 62/11:4811-4817.*

Weber et al, Poultry Science, 2003, 82/11:1701-1707.*

Weber et al, Poultry Science, 2004, 83/3:392-399.*

Ahmad, J. et al. Evaluation of a Modified-Live Virus Vaccine Administered in ovo to Protect Chickens Against Newcastle Disease, *Am. J. Vet. Res.* 153(11): 1999-2001 (1992).

Jeffers, et al., *Embryonic Response to Eimeria Tenella Infection* J. Parisitol., 56(4), 1970, 658-662.

Fredericksen, et al., *In ovo Administration of a Potential Recombinant Coccidial Antigen Vaccine in Poultry les Colloques de L'Inra*, 49, 1989, 655-660.

Perkins, Microscopic Anatomy of Invertebrates vol. 1: Protozoa, Chap. 4: "Sporozoa", 261-331, 1991, Wiley-Liss.

Proceedings of the $VI_{th}$ International Coccidosis Conference, Jun. 21-25, 1993, Guelph, Ontario, Canada, Univ. of Guelph; p. 103. Vaccine Symposium Papers.

Olson, *In situ Enzyme-Linked Immunosorbent Assay to Quantitate in vitro Development of Fimeria Tenella* Antimicrob. Agents Chemother., 34(7), Jul. 1990, 1435-39.

Sharma & Burmester, *Resistance to Marek's Disease at Hatching in Chickens Vaccinated as Embryos With Turkey Herpesvirus* Avian Diseases, 26(1), 134-148.

Hosek, et al., *Improved Method for High-Yield Exystation and Purification of Infective Sporozoites of Fimeria spp.* J. Protozool., 35(4), 1988, 583-589.

Schmatz, etal., *Purification of Fimeria Sporozoites by DE-SZ Anion Exchange Chromatography* J. Protozool., 31(1), 1984, 181-183.

Stedman's Medical Dictionary, $25^{th}$ Ed., 1990, p. 947, 1087, 1457 and 1458.

Ruff, et al., Poultry Science, 1988, 67 (Supplement I):147.

Shirley; Live Vaccines for the Control of Coccidiosis; VITH International Coccidiosis Conference, p. 61-72 (1993).

Shirley; Development of a Live Attenuated Vaccine Against Coccidiosis of Poultry; Parasite Immunology; p. 117-124 (1989).

Watkins, et al.; The Effect of in ovo Oocyst or Sporocyst Inoculation on Subsequent Coccidial Challenge; VLTH, International Coccidiosis Conference Abstract EL-2, Ontario, Canada (1993). Poultry Science 1597-1602 (1995).

R. B. Williams; The Development, Efficacy and Epidemiological Aspects of $Paracox^t$ M, A New Coccidiosis Vaccine for Chickens; Mallinckrodt Veterinary Ltd.; pp. 1-16 (1992).

Your Questions Answered; Live Attenuated Oral Coccidiosis Vaccine; Paracox, Cocci Vac®Vaccines, Cocci Vac®-T,Cocivac®-D, Cocci Vac®-B, Bursa-Vac®, Bursa-Vac®-3 and Bursa-Vac®-4; Mallinckrodt Veterinary.

The Headlines of the 80's . . . Immucox; Coccivac Brand of Coccidiosis Vaccines; Mallinkrodt Veterinary; pp. 1-11.

Immucox Coddidiosis Vaccine the Natural Solution; AAP TEK Ingredients, A Divisional of Ontario Limited; pp. 1-6.

M. W. Shirley, et al.; Live Attenuated Vaccines Against Avia Coccidiosis; Parasitology Today; vol. 13 No. 12 pp. 481-484 (1997).

* cited by examiner

IN OVO VACCINATION AGAINST COCCIDIOSIS

RELATED APPLICATION INFORMATION

This application is a continuation of U.S. Application Ser. No. 08/973,133 filed on Dec. 1, 1997 (now U.S. Pat. No. 6,500,438), which claims the benefit under 35 U.S.C. § 371 from PCT Application No. PCT/IB95/00446, filed Jun. 7, 1995 and published under PCT Article 21(2) in English, the disclosures of which are incorporated by reference herein in their entireties.

BACKGROUND OF THE INVENTION

The present invention relates to a method of vaccinating domesticated birds against coccidiosis. In particular, the invention relates to the in ovo administration of live *Eimeria* spp sporozoites or merozoites, or mixtures thereof, into the developing eggs of domesticated birds in order to immunize the hatched chicks against coccidiosis.

Coccidiosis is an enteric disease of domesticated birds caused by infection with intracellular protozoan parasites of the genus *Eimeria*. Coccidiosis is the most economically devastating parasitic disease of domesticated birds. It is estimated that anticoccidial medications and losses due to coccidiosis cost the poultry industry hundreds of millions of dollars every year.

Various attempts to vaccinate domesticated birds against coccidiosis have been reported since the early 1950's. Current vaccination methods include administering live *Eimeria* oocysts to birds through feed or water. These methods, however, are inconvenient and inefficient because not all birds get the intended oocyst dose and many are either unprotected by the vaccine or receive a pathogenic infection.

In J. M. Sharma and B. R. Burmester, Avian Dis. 26: 134–149, 1981, the authors reported that chickens vaccinated in ovo with herpesvirus of turkey developed immunity against subsequent challenge with Marek's disease virus. In European patent publication no. 291173, an immunization process is referred to wherein a nonreplicating immunogen is administered in ovo. The immunogens specifically referred to in the European patent are a genetically engineered *Eimeria* antigen and an *Eimeria* oocyst extract. The European patent specifically excludes live parasite stages such as those used in the vaccination method claimed herein.

The present vaccination method involves in ovo administration of live *Eimeria* sporozoites or merozoites, or a mixture thereof, into the developing eggs of domesticated birds. The available literature suggests that such a vaccination method would be ineffective in ovo and should be applied post-hatch. In T. K. Jeffers and G. E. Wagenbach, J. Parasit. 56(4): 656–662, 1970, the authors reported that in ovo injection of *E. tenella* sporozoites on day 10 of incubation provided no significant immunological protection against subsequent challenge with *E. tenella* oocysts. In fact, they reported that chicks that received no treatment had a greater survival rate against subsequent challenge with *E. tenella* oocysts than chicks that had been treated in ovo with sporozoites. In K. L. Watkins et al., Proc. VI th. International Coccidiosis Conf., Abstract E1–2, Ontario, Canada, 1993, the authors described in ovo inoculation with live *E. maxima* sporocysts and sporulated oocysts and concluded that their study provided no evidence that in ovo exposure protects against subsequent coccidial challenge with *E. maxima* oocysts 10 days post-hatch. Watkins et al. further concluded that significant immunological protection is provided if inoculation is done soon after hatch rather than in ovo. Contrary to this teaching, the in ovo vaccination method of the present invention provides unexpected immunity that protects the hatched birds against subsequent coccidial challenge.

SUMMARY OF THE INVENTION

The present invention, also referred to herein as the "present vaccination method", relates to a method of vaccinating a domesticated bird against coccidiosis comprising administering in ovo, during the final quarter of incubation, an effective immunizing dose of live *Eimeria* sporozoites or merozoites, or a mixture thereof.

The term "domesticated bird(s)", as used herein, unless otherwise indicated, includes chickens, turkeys, ducks, game birds (including, but not limited to, quail, pheasants, and geese) and ratites (including, but not limited to, ostrich).

The term "in ovo", as used herein, unless otherwise indicated, means into a domesticated bird egg containing a live, developing embryo.

The term "administering in ovo" or "in ovo administration", as used herein, unless otherwise indicated, means administering the vaccine described herein to a domesticated bird egg containing a live, developing embryo by any means of penetrating the shell of the egg and introducing the vaccine. Such means of administration include, but are not limited to, injection of the vaccine.

The term "final quarter of incubation", as used herein, unless otherwise indicated, means the final quarter of incubation of a developing egg of a domesticated bird.

The term "*Eimeria*", as used herein, unless otherwise indicated, means one or more species of the genus *Eimeria* that infect domesticated birds. Such *Eimeria* species include those that are found in chicken, including *E. tenella*, *E. acervulina*, *E. maxima*, *E. necatrix*, *E. mitis*, *E. praecox*, and *E. brunetti*, and also those that are found in turkeys, including *E. meleagrimitis*, *E. adenoeides*, *E. gallopavonis*, *E. dispersa*, *E. meleagridis*, *E. innocua*, and *E. subrotunda*, and also *Eimeria* species that infect other domesticated birds as defined above. The term "*Eimeria*" also includes all strains of the foregoing species of *Eimeria*, including, but not limited to, precocious strains, and attenuated strains, which includes strains that have been irradiated, or otherwise treated, so that they fail to complete development. The term *Eimeria* also includes any newly-discovered strains or species of *Eimeria* that infect domesticated birds as defined above.

The terms "sporozoites", "sporocysts", "oocysts", and "merozoites", as used herein, unless otherwise indicated, mean live *Eimeria* sporozoites, sporocysts, oocysts, and merozoites.

The term "effective immunizing dose", as used herein, unless otherwise indicated, means a number of sporozoites or merozoites, or, when mixed, a number of sporozoites and merozoites, sufficient to provide immunological protection in the hatched birds that is greater than the inherent immunity of non-immunized birds. As used herein, the terms "immunize" and "vaccinate" are synonymous and are used interchangeably.

A preferred dose to be administered in accord with the method of the invention comprises 10 to $10^5$ sporozoites or merozoites, or a mixture thereof wherein the total number of said sporozoites and merozoites ranges from 10 to $10^5$.

A more preferred dose comprises $10^3$ to $10^6$ sporozoite or merozoites, or a mixture thereof wherein the total number of said sporozoites and merozoites ranges from $10^3$ to $10^6$.

Another preferred dose comprises $10^2$ to $10^5$ sporozoites or merozoites, or a mixture thereof wherein the total number of said sporozoites and merozoites ranges from $10^2$ to $10^5$.

A preferred domesticated bird to be vaccinated in accord with the method of the invention is a chicken.

A preferred dose to be administered in ovo to chicken eggs comprises sporozoites or merozoites, or a mixture thereof, of two or more species of *Eimeria* selected from the group consisting of *E. tenella, E. acervulina, E. maxima, E. necatrix, E. mitis, E. praecox,* and *E. brunetti*. The dose preferably includes from 10 to $10^6$ sporozoites or merozoites, or a mixture thereof, for each species that is included in the dose.

Another preferred domesticated bird to be vaccinated in accord with the method of the invention is a turkey.

A preferred dose to be administered in ovo to turkey eggs comprises sporozoites or merozoites, or a mixture thereof, of two or more species of *Eimeria* selected from the group consisting of *E. meleagrimitis, E. adenoeides, E. gallopavonis, E. dispersa, E. meleagridis, E. innocua,* and *E. subrotunda*. The dose preferably includes from 10 to $10^6$ sporozoites or merozoites, or a mixture thereof, for each species that is included in the dose.

Other preferred domesticated birds to be vaccinated in accord with the method of the invention are game birds, ducks and ratites.

The method of the invention further comprises, in combination with the present vaccination method, administering in ovo an immune stimulant at any time during incubation.

A preferred method of administering the immune stimulant is simultaneously with the in ovo administration of a dose of sporozoites or merozoites, or mixture of said sporozoites and merozoites, during the final quarter of incubation.

DETAILED DESCRIPTION OF THE INVENTION

The present vaccination method involves the in ovo administration, during the final quarter of incubation, of live *Eimeria* sporozoites or merozoites, or a mixture thereof, into domesticated birds' eggs. In the case of chickens, in ovo administration is preferably done on days 15–20 of incubation, and most preferably on day 18 of incubation. In the case of turkeys, in ovo administration is preferably done on days 21–26 of incubation.

The present vaccination method can be performed using any suitable in ovo administration method. Preferably, the present vaccine is administered via injection. According to one method of injection, a hole is made in the egg shell at the large end of the egg using an 18 guage needle to expose the egg's air cell. A 1.0–1.5 inch 22 guage needle attached to a syringe of appropriate size (1–3 ml) can be inserted through the hole and through the membrane of the air cell. An appropriate number of sporozoites or merozoites, or, when mixed, an appropriate number of sporozoites and merozoites, are suspended in a suitable liquid carrier, for instance 10–500 µl of phosphate-buffered saline, and then injected into the egg. The appropriate volume will depend on the size of the egg being treated, with ostrich eggs obviously being capable of taking more volume than chicken eggs. The site of injection can be within any region of the egg or embryo. Preferably, injection is done axially through the center of the large end of the egg into the amnion.

Alternatively, an automated egg injection system can be used in the present vaccination method. Such systems are described in U.S. Pat. Nos. 4,681,063, 4,040,388, 4,469,047, and 4,593,646, which are herein incorporated by reference. Other appropriate methods of injection are known to those skilled in the art.

Oocysts can be prepared by any of several methods known to those skilled in the art. Such methods include those described in J. F. Ryley et al., Parasitology 73:311–326, 1976 and P. L. Long et al., Folia Veterinaria Latina VI#3, 201–217, 1976, which are herein incorporated by reference. According to one method, commercial broiler chickens, approximately 2 weeks old, are infected with the *Eimera* species of interest by oral gavage of an appropriate dose of sporulated oocysts. For example, a typical dose used for *E. tenella* is 200,000 sporulated oocysts/bird. Well known procedures for collection and purification of oocysts from infected birds are then followed. For most species of *Eimeria*, feces are collected from infected birds 5–7 days post-infection, blended and filtered to remove debris, then centrifuged at a speed sufficient to pellet the remaining fecal material. For *E. tenella*, a similar procedure is used except that cecal cores are taken at 6 days post-infection. The pellet is resuspended in a saturated salt solution, in which the oocysts float and most of the contaminating debris can be removed by centrifugation. The oocyst suspension is then diluted to lower the salt concentration. The oocysts are washed repeatedly to remove the salt and resuspended in potassium dichromate solution (2.5% w/v). The oocyst suspension is incubated at 29° C. with shaking (e.g., 140 rpm) for approximately 72 hours to induce sporulation of the oocysts. Alternatively, the oocysts can be treated with sodium hypochlorite and then sporulated. The number of sporulated oocyst/ml is determined by direct count using a hemocytometer, and the culture is stored, preferably under refrigeration until needed.

To prepare sporocysts, the potassium dichromate is removed from the oocyst suspension described above by repeated washing of the oocysts, which involves collection of oocysts by centrifugation and resuspending in deionized or distilled water. When the dichromate has been removed as judged by the lack of yellowish-orange coloration, the oocyst suspension is mixed with an equal volume of sodium hypochlorite (bleach) and incubated at room temperature for 15 minutes. The bleach is then removed by repeated washings, and the oocysts are resuspended in physiological saline or deionized water. Oocysts can be broken to release sporocysts using a variety of known techniques. For example, oocysts can be broken to release sporocysts by mixing the oocysts with glass beads of 1–4 mm diameter and shaking by hand, vortex mixer, or shaking incubator, or using a hand-held homogenizer. Unbroken oocysts and oocysts walls can be separated from the released sporocysts by differential centrifugation in 50% PERCOLL, a colloidal suspension of polyvinyl pyrrolidone coated silica particles (sold by Pharmacia Biotech) or 1 M sucrose as described in Dulski et al., Avian Diseases, 32: 235–239, 1988.

To prepare sporozoites or a sporozoite-rich preparation to be used in accord with the present invention sporozoites are excysted from the sporocyst preparation described above. In one procedure, sporocysts prepared as described above are pelleted by centrifugation, resuspended in excystation buffer (0.5% taurodeoxycholic acid and 0.25% trypsin in phosphate buffered saline, pH 8.0) and incubated with shaking for one hour at 41° C. A sample of the resulting suspension is counted to determine the number of sporozoites, the sporozoites are washed once to remove the excystation buffer, and resuspended in phosphate-buffered saline at the desired concentration for in ovo injection. This preparation contains sporozoites, sporocysts and oocysts, and, without further purification, can be used in accord with the present vaccination method. Purified sporozoites, removed from sporocysts and oocysts, can be prepared by DE-52 anion exchange chromatography as described in D. M. Schmatz et al., J. Protozool. 31: 181–183, 1984, which is herein incorporated by reference. The dose of sporozoites to be used in the present vaccination method will vary according to the type of domesticated bird being vaccinated and the species of Eimeria being used in the vaccine. In general, the dose can range from 10 to $10^6$ sporozoites per egg. Preferably, the dose ranges from 10 to $10^5$ sporozoites per egg, and, more preferably, the dose ranges from $10^2$ to $10^5$ sporozoites per egg.

Merozoites can be prepared by various methods known to those skilled in the art. In one method, sporozoites are infected into primary chick kidney cells (PCK) that are grown in culture as cell aggregates, using a modification of the method described in D. J. Doran, J. Parasit. 57: 891–900, 1971, which is herein incorporated by reference. PCK cells are grown at 40° C. in 3% $CO_2$ in modified RK2 medium—DMEM/F12 with L-glutamine and 15 mM HEPES, supplemented with fetal bovine serum, penicillin-streptomycin, 15 mM sodium bicarbonate, 10 ng/ml epidermal growth factor, 5 μg/ml insulin, 5 μg/ml transferrin, 5 ng/ml selenious acid and 0.01 μM hydrocortisone HCL as described in S. D. Chung et al., J. Cell Biol. 95: 118–126, 1982. PCK cells are prepared from kidneys of 2 to 3 week old chicks by mincing the kidney, and then treating the tissue at 37° C. with several changes of 0.2 mg/ml collagenase (sold by Worthington Biochemical Corp., Freehold, N.J.) in phosphate-buffered saline solution. The cellular aggregates in the supernatant are washed, resuspended in modified RK2 medium containing 5% fetal bovine serum and used to seed tissue cultures flasks at a density of $10^5$ aggregates per $cm^2$. The PCK cells are incubated for 18 hours at 40° C. in 3% $CO_2$ and then infected with $4 \times 10^5$ sporozoites/$cm^2$. Infected cultures are grown in modified RK2 medium containing 2% fetal bovine serum. After 24 hours of incubation, to allow invasion, uninvaded sporozoites are removed by agitating the flask and removing the culture medium. The cell layer is washed once with modified RK2 medium containing 2% fetal bovine serum and the culture medium is again discarded. Fresh RK2 medium is added, and the cultures are incubated for another 48 to 54 hours until merozoites are released into the culture medium.

Purification of the merozoites to remove host cell debris can be done by various methods known to those skilled in the art. In accord with one method, as described in J. A. Olson, Antimicrob. Agents Chemother. 34: 1435–1439, 1990, the culture medium containing the released merozoites is collected and spun at 450×g for 10 minutes to concentrate the merozoites. The pellet containing the merozoites and the host cell debris is suspended in 0.1 M NaCl-0.05 M KCl-20% bovine serum albumin and applied to a DE-52 anion exchange column equilibrated in 75 mM Tris-40 mM $NaH_2PO_4$-86 mM NaCl-100 mM glucose at pH 8.2. Merozoites flow through the column. Merozoites collected from the column can be tested for purity by electron microscopy as described in A. Kilejian, J. Biol. Chem. 249: 4650–4655, 1974. In general, the merozoite dose can range from 10 to $10^6$ merozoites per egg. Preferably, the dose ranges from 10 to $10^5$ merozoites per egg, and, more preferably, the dose ranges from $10^2$ to $10^5$ merozoites per egg. When sporozoites and merozoites are mixed, in general, the dose comprising the total number of merozoites and sporozoites can range from 10 to $10^6$ per egg. Preferably, the dose ranges from 10 to $10^5$ merozoites and sporozoites per egg, and, more preferably, the dose ranges from $10^2$ to $10^5$ merozoites and sporozoites per egg.

The sporozoites or merozoites, or mixture thereof, can be injected in ovo in any physiologically suitable medium. Preferably, they are suspended in physiologically balanced saline such as phosphate-buffered saline. The selected medium can optionally include one or more suspending agents including physiologically suitable gels, gelatins, hydrosols, cellulose, or polysaccharide gums.

Preferably, in the present vaccination method, sporozoites or merozoites, or a mixture thereof, of two or more Eimeria species are injected in ovo at the same time. In accord with the present vaccination method, sporozoites or merozoites, or a mixture thereof, of all identified species of Eimeria that infect a specific domesticated bird, such as chicken, can be injected in ovo at the same time, or in series, at appropriate doses to provide immunological protection against all species.

Immune stimulants can be used in conjunction with the present vaccination method. Suitable immune stimulants include, but are not limited to, cytokines, growth factors, chemokines, supernatants from cell cultures of lymphocytes, monocytes, or cells from lymphoid organs, cell preparation or cell extracts (e.g. *Staphylococcus aureus* or lipopolysaccharide preparations), mitogens, or adjuvants including low molecular weight pharmaceuticals. An immune stimulant can be administered in ovo at any time during incubation. Preferably, an immune stimulant is administered in ovo in the medium containing the dose of Eimeria sporozoites or merozoites, or mixture thereof.

The efficacy of the present invention in vaccinating against coccidiosis is illustrated in the following examples. Each dose was injected in ovo in physiologically-acceptable saline as described above. The effectiveness of a particular preparation was determined by monitoring its effect on hatch rate and hatch weight of the chicks, and, following challenge infection, oocyst production, weight gain, and pathogenicity (lesion score). Lesion scores were assigned according to the protocol described in J. K. Johnson and W. M. Reid, Exp. Parasitol. 28: 30–36, 1970, according to which a value of 0 represents no disease and a value of 4 represents maximum pathology.

EXAMPLE 1

Chicken eggs were injected on day 18 of incubation with a preparation containing $10^5$ E. tenella sporozoites per egg. The preparation was not purified to remove sporocysts and oocysts. Each dose also contained approximately $10^4$ E. tenella sporocysts and approximately $10^4$ E. tenella oocysts. As a control, eggs were injected only with phosphate-buffered saline solution. In the sporozoite-treated population of birds the mean oocyst shed at 7 days post-hatch was $1.1 \times 10^6$ oocysts/bird. Non-immunized birds and the sporozoite-treated birds were challenged with various doses of sporulated oocysts of E. tenella, administered by oral gavage, on days 7, 14 or 21 post-hatch. The data appear in Table 1.

Immunized Versus Non-Immunized Birds:
Responses to Different Challenge Doses at
Different Times Post-Hatch their non-immunized hatch mates in terms of hatch rate and hatch weight. The chicks were then challenged on day 14 post-hatch with $1.25 \times 10^4$ sporulated oocysts of E. tenella

TABLE 1

| Group[1] | Challenge dose (sporulated oocysts per bird) | Lesion score on sixth day after challenge | | Weight gain (grams) per bird over six day period after challenge | |
|---|---|---|---|---|---|
| | | Non-immunized | Immunized In Ovo ($10^5$ sporozoites on day 18 of incubation) | Non-immunized | Immunized In Ovo ($10^5$ sporozoites on day 18 of incubation) |
| Challenge on day 7 post-hatch | 0 | 0 | 0 | 188 | 167 |
| | $2.5 \times 10^3$ | 3.0 | 0.3* | 154 | 153 |
| | $5 \times 10^3$ | 3.1 | 1.2* | 153 | 167 |
| | $1 \times 10^4$ | 3.7 | 1.4* | 123 | 165* |
| Challenge on day 14 post-hatch | 0 | 0 | 0 | 266 | 278 |
| | $2.5 \times 10^3$ | 2.4 | 0.4* | 260 | 269 |
| | $5 \times 10^3$ | 2.8 | 1.1* | 244 | 265 |
| | $1 \times 10^4$ | 3.3 | 1.6* | 235 | 259 |
| Challenge on day 21 post-hatch | 0 | 0.1 | 0 | 361 | 357 |
| | $2.5 \times 10^3$ | 2.3 | 0.7* | 375 | 358 |
| | $5 \times 10^3$ | 2.1 | 0.8* | 332 | 344 |
| | $1 \times 10^4$ | 2.8 | 1.4* | 337 | 395* |

[1]Each group was subjected to a single challenge of sporulated oocysts on days 7, 14, or 21 post-hatch. For example, birds challenged on day 21 post-hatch were not challenged on days 7 or 14 post-hatch.
*Significantly different from non-immunized birds (p < 0.05, ANOVA)

The data in Table 1 clearly show that the immunized birds were less susceptible to infection than their non-immunized hatch mates as indicated by the reduced lesion scores and improved weight gains in the immunized birds. The data also demonstrate that the method of the invention imparts immunity to the chicks at a relatively early age (within seven days post-hatch). Furthermore, the data show that the immunity continues as the chicks grow and develop. Imparting immunity to chicks at an early age provides a significant advantage in the broiler chicken industry because broilers routinely reach market by 6 weeks of age.

EXAMPLE 2

Chicken eggs were injected on day 18 of incubation with saline (control) or preparations containing different doses of sporozoites of E. tenella, as indicated in Table 2 which provides the pre-challenge results. The sporozoite preparation used for each dose contained 62% sporozoites, 9% sporocysts, and 29% oocysts. Each dose containing $10^5$ sporozoites included a total of $1.6 \times 10^5$ parasite stages (sporozoites, sporocysts, and oocysts).

Effect of in ovo Vaccination on Hatch Rate and Weight

TABLE 2

| Sporozoites injected per egg on day 18 of incubation | Hatch rate (%) | Hatch weight (grams) |
|---|---|---|
| 0 | 94 | 48.2 |
| 0 | 94 | 48.0 |
| $10^3$ | 100 | 49.4 |
| $10^4$ | 97 | 47.0 |
| $10^5$ | 94 | 49.1 |

The data in Table 2 show that chicks hatched from eggs injected with live sporozoites were substantially identical to per bird, administered by oral gavage. The post-challenge results are provided in Table 3.

Response to Challenge Infection of
Non-Immunized Birds Versus Birds Treated in ovo
with Different Doses of Sporozoites

TABLE 3

| Sporozoites injected per egg on day 18 of incubation | Weight Gain per bird over six day period after challenge | Lesion Score on day 6 after challenge | Oocysts shed per bird ($\times 10^6$) on day 6 after challenge |
|---|---|---|---|
| 0 | 278 | 3.2 | 12.3 |
| 0 (Unchallenged control) | 321 | 0 | 0.003* |
| $10^3$ | 289 | 2.6* | 11.2 |
| $10^4$ | 291 | 2.7 | 12.2 |
| $10^5$ | 304* | 1.4* | 1.4* |

*Significantly different from non-immunized group (received saline) that was subjected to challenge (p < 0.05, ANOVA)

The data in Table 3 show that for every parameter (weight gain, lesion score, oocyst shed) chicks hatched from eggs injected with different doses of the sporozoite preparation showed evidence of immunity. In comparison to the control birds that were treated only with saline and were subjected to challenge infection, the birds immunized in ovo with the sporozoite preparation showed greater weight gain and reduced lesion scores. In addition, the birds immunized in ovo with the sporozoite preparation passed fewer oocysts than the control birds after challenge infection, indicating that the infection was less severe in the immunized birds.

We claim:
1. A method of vaccinating a chicken against coccidiosis comprising administering in ovo, during the final quarter of incubation, an effective immunizing dose of live *Eimeria* sporozoites, wherein the dose is administered by in ovo injection.

2. The method of claim 1 wherein the dose further comprises live *Eimeria* merozoites.

3. The method of claim 1 wherein the dose is administered to the amnion.

4. The method of claim 3 wherein the dose is administered axially through the large end of the egg into the amnion.

5. The method of claim 1 wherein the dose is administered from day 15 to day 20 of incubation.

6. The method of claim 5 wherein the dose is administered on day 18 of incubation.

7. The method of claim 1 wherein the dose comprises 10 to $10^6$ sporozoites.

8. The method of claim 1 wherein the dose comprises $10^3$ to $10^5$ sporozoites.

9. The method of claim 1 wherein the dose comprises $10^2$ to $10^5$ sporozoites.

10. The method of claim 1 wherein the dose comprises sporozoites of two or more species of *Eimeria* selected from the group consisting of *E. tenella, E. acervulina, E. maxima, E. necatrix, E. mitis, E. praecox,* and *E. brunetti.*

11. The method of claim 1 further comprising administering in ovo an immune stimulant at any time during incubation.

12. The method of claim 11 wherein the immune stimulant is administered in ovo simultaneously with the dose of sporozoites.

13. The method or claim 1 wherein the sporozoites have been purified to remove sporocysts and oocysts.

14. A method of vaccinating a chicken against coccidiosis comprising administering in ovo, during the final quarter of incubation, an effective immunizing dose of live *Eimeria* merozoites, wherein the dose is administered by in ovo injection.

15. The method of claim 14 wherein the dose is administered to the amnion.

16. The method of claim 14 wherein the dose is administered axially through the large end of the egg into the amnion.

17. The method of claim 14 wherein the dose is administered from day 15 to day 20 of incubation.

18. The method of claim 17 wherein the dose is administered on day 18 of incubation.

19. The method of claim 14 wherein the dose comprises 10 to $10^6$ merozoites.

20. The method of claim 14 wherein the dose comprises $10^3$ to $10^6$ merozoites.

21. The method of claim 14 wherein the dose comprises $10^2$ to $10^5$ merozoites.

22. The method of claim 14 wherein the dose comprises merozoites of two or more species of *Eimeria* selected from the group consisting of *E. tenella, E. acervulina, E. maxima, E. necatrix, E. mitis, E. praecox,* and *E. brunetti.*

23. The method of claim 14 further comprising administering in ovo an immune stimulant at any time during incubation.

24. The method of claim 23 wherein the immune stimulant is administered in ovo simultaneously with the dose of merozoites.

\* \* \* \* \*

UNITED STATES PATENT AND TRADEMARK OFFICE
CERTIFICATE OF CORRECTION

PATENT NO. : 7,018,640 B2  Page 1 of 1
APPLICATION NO. : 10/094436
DATED : March 28, 2006
INVENTOR(S) : Evans et al.

It is certified that error appears in the above-identified patent and that said Letters Patent is hereby corrected as shown below:

Column 9
Line 17 should read -- to $10^6$ sporozoites. --

Line 30 should read -- 13. The method of claim 1 wherein the sporozoites have --

Signed and Sealed this

Nineteenth Day of September, 2006

JON W. DUDAS
*Director of the United States Patent and Trademark Office*